(12) United States Patent
Hoefig et al.

(10) Patent No.: US 7,553,277 B2
(45) Date of Patent: Jun. 30, 2009

(54) ENDOSCOPE WITH VARIABLE DIRECTION OF VIEW

(75) Inventors: Siegfried Hoefig, Muehlheim (DE); Fang Lei, Durchhausen (DE)

(73) Assignee: Karl Storz GmbH & Co. KG (DE)

( * ) Notice: Subject to any disclaimer, the term of this patent is extended or adjusted under 35 U.S.C. 154(b) by 308 days.

(21) Appl. No.: 11/512,548

(22) Filed: Aug. 30, 2006

(65) Prior Publication Data

US 2007/0055103 A1 Mar. 8, 2007

(30) Foreign Application Priority Data

Aug. 31, 2005 (EP) .................. 05018933

(51) Int. Cl.
*A61B 1/008* (2006.01)
(52) U.S. Cl. ............. 600/173; 600/137; 600/142; 600/152
(58) Field of Classification Search ............ 600/173, 600/142, 146, 152, 137; 348/82–85; 165/11.2
See application file for complete search history.

(56) References Cited

U.S. PATENT DOCUMENTS

| | | | | |
|---|---|---|---|---|
| 3,557,780 A | * | 1/1971 | Sato | 600/141 |
| 4,832,473 A | * | 5/1989 | Ueda | 359/367 |
| 4,855,838 A | * | 8/1989 | Jones et al. | 348/84 |
| 5,179,934 A | | 1/1993 | Nagayoshi et al. | 128/4 |
| 5,179,935 A | * | 1/1993 | Miyagi | 600/142 |
| 5,512,034 A | * | 4/1996 | Finn et al. | 600/138 |
| 5,617,762 A | * | 4/1997 | Kirsch | 74/490.06 |
| 5,762,603 A | | 6/1998 | Thompson | 600/112 |
| 5,810,716 A | * | 9/1998 | Mukherjee et al. | 600/146 |
| 5,956,077 A | * | 9/1999 | Qureshi et al. | 348/82 |
| 5,989,182 A | * | 11/1999 | Hori et al. | 600/112 |
| 6,277,064 B1 | * | 8/2001 | Yoon | 600/114 |
| 6,371,909 B1 | | 4/2002 | Hoeg et al. | 600/173 |
| 6,393,338 B1 | * | 5/2002 | Kemnitz | 700/231 |
| 6,428,470 B1 | * | 8/2002 | Thompson | 600/173 |
| 6,500,115 B2 | | 12/2002 | Krattiger et al. | 600/173 |
| 6,656,112 B2 | * | 12/2003 | Miyanaga | 600/179 |
| 2001/0023313 A1 | | 9/2001 | Ide | 600/142 |

(Continued)

FOREIGN PATENT DOCUMENTS

WO    WO 03/086179    10/2003

OTHER PUBLICATIONS

European Search Report; Feb. 10, 2006; 8 pages.

*Primary Examiner*—John P Leubecker
(74) *Attorney, Agent, or Firm*—St. Onge Steward Johnston & Reens LLC (57) ABSTRACT

An endoscope, comprising an elongated rigid shaft and an optical imaging system arranged at a distal end of the shaft for receiving light from an observation area, wherein the optical imaging system is pivotable with respect to the shaft about a first pivot axis which runs about transversely to a longitudinal axis of the shaft. The optical imaging system is pivotable with respect to the shaft about at least a second pivot axis, which is spaced from the first pivot axis and runs about transversely to the longitudinal axis of the shaft, and an overall pivot range of the optical imaging system about the first and at least second pivot axis is at least 150° from the longitudinal axis of the shaft.

25 Claims, 9 Drawing Sheets

U.S. PATENT DOCUMENTS

| | | | |
|---|---|---|---|
| 2003/0032863 A1 | 2/2003 | Kazakevich | 600/173 |
| 2003/0092966 A1 | 5/2003 | Schara et al. | 600/173 |
| 2004/0215061 A1* | 10/2004 | Kimmel et al. | 600/179 |
| 2005/0234296 A1* | 10/2005 | Saadat et al. | 600/129 |
| 2006/0252994 A1* | 11/2006 | Ratnakar | 600/173 |

* cited by examiner

ENDOSCOPE WITH VARIABLE DIRECTION OF VIEW

CROSS REFERENCE TO RELATED APPLICATION

The present application claims priority of European patent application no. 05 018 933.1 filed on Aug. 31, 2005.

BACKGROUND OF THE INVENTION

The invention relates to an endoscope, comprising an elongated shaft and an optical imaging system arranged at a substantially rigid distal end of the shaft for receiving light from an observation area, wherein the optical imaging system is pivotable with respect to the shaft about a first pivot axis which runs about transversely to a longitudinal axis of the shaft.

Endoscopes are used for medical, in particular surgical purposes and for industrial purposes.

In medical procedures, endoscopes are used in minimally-invasive surgery, such as laparoscopic, hysteroscopic, and arthroscopic surgery which is becoming more widely used because it is often less traumatic to the patient. Endoscopes are not only utilized for surgical procedures, but are also utilized as a pure observation instrument for assisting a physician to accurately place medical equipment into a body cavity.

In industrial applications, endoscopes are, for example, used to inspect cavities in machines or machine parts, or they are used to observe dynamic processes in, for example, internal combustion engines.

The present invention is applicable to endoscopes for medical purposes as well as for endoscopes for industrial purposes.

An endoscope enables a person to remotely view an observation area. To this end, an endoscope comprises an optical imaging system arranged at a distal end of the shaft for receiving light from the observation area.

The optical imaging system typically comprises an objective lens arrangement or light entrance window which determines the direction of view of the endoscope. The optical imaging system can further comprise an electronic image pick-up, for example a charged coupled device (CCD) chip, which is also arranged at the distal end of the endoscope shaft proximally to the objective lens arrangement.

Most conventional endoscopes having a rigid shaft provide a limited and fixed direction of view so that in case of a medical endoscope, the surgeon typically must physically reposition the entire endoscope in order to change the endoscopic view within the body cavity, or remove the endoscope entirely and replace it with one having the desired angle of view. Such manipulations and replacements can be undesirable, since they can complicate the surgery and increase the risk of inadvertent damage to body tissue from accidental contact between the tissue and the endoscope.

Therefore, several designs have been proposed to permit individual endoscopes to vary their angles of view without requiring extensive movement of the endoscope. The small sizes of endoscopes, which can be in the order of 3 mm in diameter, place restrictions on such designs, and limit the options available.

An endoscope known from document WO 03/086179A1 has an elongated rigid shaft provided at the distal end thereof with an optical imaging system which is supported on a mobile head. The mobile head and, thus, the optical imaging system, is pivotable with respect to the shaft about a pivot axis which runs about transversely to a longitudinal axis of the shaft.

In the 0° position of the mobile head, the direction of view of the optical imaging system lies on the longitudinal axis of the shaft, thus allowing a straight ahead view. In order to change the direction of view, the mobile head can be pivoted about the pivot axis in one plane which includes the longitudinal axis of the shaft.

A drawback of this known endoscope is that the mobile head is pivotable about the pivot axis by an angle of about 90° at most. Thus, this known endoscope is not suited to allow directions of view which are directed backward with respect to the distal end of the endoscope shaft. In order to observe an object in the observation area which is situated behind the distal end of the endoscope shaft, it is, therefore, necessary to draw the endoscope back or to replace the endoscope with an endoscope for backward viewing. As already mentioned, such a displacement or replacement of the endoscope can be undesirable.

Another endoscope having a variable direction of view is disclosed in US 2003/0092966 A1. This known endoscope comprises a rigid shaft having a glass housing mounted at the distal end of the shaft and which is arranged off-axis with respect to the longitudinal axis of the shaft. An optical imaging system is arranged in the housing. By means of a control mechanism having an electrical motor and a gear, the optical imaging system can be rotated about a rotation axis perpendicular to the longitudinal axis of the shaft. While this design renders it possible to adjust a direction of view in 180° (backward) direction with respect to the longitudinal axis, this design has the drawback that the line of sight in 0° direction is offset with respect to the longitudinal axis of the shaft. Such an offset between the line of sight in 0° direction and the longitudinal axis requires a certain habituation to the use of this known endoscope.

Further, U.S. Pat. No. 6,371,909 B1 discloses a variable direction-of-view endoscope. According to one embodiment disclosed in this document, the endoscope comprises an optical imaging system at the distal end of the endoscope shaft, wherein the optical imaging system is pivotable about a pivot axis which runs about transversely to the longitudinal axis of the shaft. Nevertheless, the pivoting movement of the optical imaging system is limited to angles of view in the range from 0° to about ±150°.

There are also known endoscopes having a flexible shaft rather than a rigid shaft. Such flexible endoscopes usually have a control mechanism for bending the distal region of the flexible shaft, and by virtue of the flexibility of the shaft allow angles of view in a plane in the range from 0° to 180°. The control mechanism of such flexible endoscopes, however, consists of a pullwire mechanism which is cost-intensive in terms of manufacture. Further, a conventional flexible endoscope needs space in the distal region when the distal end of the shaft is bended back. This is because the bending radius cannot be made as small as desired due to glass fibers used for the imaging system of such a flexible endoscope.

SUMMARY OF THE INVENTION

It is an object of the present invention to improve an endoscope as mentioned at the outset in such a way that the range of possible angles of view is enlarged without increasing the space needed in the observation area for the increased range of directions of view.

According to the present invention, an endoscope is provided, comprising an elongated shaft having a substantially_ rigid distal end and a longitudinal axis. An optical imaging system is arranged at the distal end of the shaft for receiving light from an observation area. The optical imaging system is pivotable with respect to the shaft about a first pivot axis running about transversely to the longitudinal axis of the shaft. The optical imaging system is pivotable with respect to the shaft about at least a second pivot axis spaced from the first pivot axis and running about transversely to the longitudinal axis of the shaft. An overall pivot range of the optical imaging system about the first and the at least second pivot axis is at least 150° from the longitudinal axis of the shaft.

The endoscope according to the present invention has at least two well defined pivot axes which are spaced from one another in the longitudinal direction of the shaft and about which the optical imaging system can be pivoted such that the single pivot ranges of the optical imaging system about the first and second pivot axis add up to an overall pivot range which is larger than the single pivot ranges themselves. The provision of the at least one second pivot axis in a distance from the third pivot axis renders it possible to achieve directions of view even in the range from 0° to about 180° or more, and further ensures that the 0° direction of view is aligned with the longitudinal axis of the shaft, i.e. is not offset with respect to same. Thus, an enhanced range of angles of view can be achieved with the present Invention. The present invention can be used in endoscopes having a rigid shaft as well as in endoscopes having a semi-flexible or flexible shaft, where it is advantageous that the change of direction of view is no longer based on a bending action, but on a pivoting movement about two well defined fixed pivot axes.

In a preferred refinement, the overall pivot range is at least about 180° from the longitudinal axis of the shaft.

The advantage of this measure is that a backward view direction substantially parallel to the longitudinal axis of the shaft can be obtained. Thus, it is possible to observe the backside of a structure in a recess of the observation area.

In a further preferred refinement, the optical imaging system is pivotable about the first and/or at least one second pivot axis from the longitudinal axis in opposite directions.

The advantage here is that the overall pivot range of the optical imaging system about the first and at least one second pivot axis is still increased, for example in connection with the refinement mentioned before an overall pivot range of ±180° can be achieved.

In a further preferred refinement, the optical imaging system is pivotable about the first pivot axis in a range of at least about 70° to about 110° and about the at least one second pivot axis in a range of at least about 40° to about 110°.

In this way, the pivot ranges of the optical imaging system about the first and at least one second pivot axis add up to an overall pivot range of at least 150° from the longitudinal axis of the shaft. In a preferred embodiment, the pivot range about the first pivot axis and the at least one second pivot axis is approximately at least 90° in each case.

In a further preferred refinement, the first pivot axis and the at least one second pivot axis are about parallel with respect to one another.

The advantage of this measure is that the overall range of directions of view lie in the same plane when the optical imaging system is pivoted about the first pivot axis and additionally about the second pivot axis. Thus, when the optical imaging system is pivoted about the first pivot axis and then about the second pivot axis, the line of sight is swept through the same plane.

In a further preferred refinement, the optical imaging system is at least partially arranged in a distal head which is pivotably mounted on a first shaft portion to be pivotable about the first pivot axis, which first shaft portion in turn is pivotably mounted on a second shaft portion to be pivotable about the at least one second pivot axis.

In this configuration, the distal region of the endoscope according to the invention comprises at least three parts which are articulatedly connected to one another. The joints between the distal head, the first shaft portion and the second shaft portion can advantageously be formed by pins or the like in order to obtain defined first and at least one second pivot axes without the need for flexible elements which could be too weak to withstand a large number of bending operations.

In this context, it is preferred if the distal head has a substantially ball-shaped housing.

The advantage here is that the distal head which forms the outermost distal end of the endoscope, does not represent edges or the like and, therefore, does not cause the risk of tissue damages in case the endoscope according to the invention is used as a medical endoscope for observing a body cavity, when the optical imaging system is pivoted about the first and/or at least one second pivot axis.

In a further preferred refinement, the optical imaging system comprises an electronic image pick-up and an imaging optics for imaging an object to be viewed onto the image pick-up, the image pick-up and the imaging optics being arranged in the distal head.

The advantage of this measure is that the entire optical imaging system is arranged in the distal head and is pivoted about the first pivot axis and the at least one second pivot axis as a whole, thus avoiding complicated optical arrangements in order to pass the light through the pivotable regions of the endoscope according to different pivot angles about the first and/or at least one second pivot axis. In contrast, it is only necessary to provide electrical lines which are fed through the articulations between the distal heads, the first shaft portion and the second shaft portion in order to lead the signals produced by the image pick-up to the proximal ends of the endoscope, or, the signal transfer from the image pick-up to the proximal region to the endoscope can be more preferably realized by means of sliding contacts or still more preferably with the aid of radio signals produced by the image pick-up. In the latter case, transponder technique can be used in order to realize a transmission of the image pick-up signals to the proximal region of the endoscope. One or more receiver coils can be arranged in the distal head for receiving inductively coupled-in energy and control signals, and a transmission system which transmits image signals from the image pick-up outwards for further processing.

In a further preferred refinement, the optical imaging system is rotatable about the longitudinal axis of the shaft.

This measure is in particular advantageous, because the overall range of directions of view is still increased without the need to rotate the endoscope about the longitudinal axis of the shaft. In connection with the pivoting movement of the optical imaging system about the first and at least one second pivot axis, in particular if the overall pivot range is at least about 180° from the longitudinal axis of the shaft as mentioned before in connection with one preferred refinement, the optical imaging system and thus the direction of view can be swept through nearly the entire solid angle of $4\pi$, if, as provided in a further preferred refinement, the range of rotation of the optical imaging system about the longitudinal axis of the shaft is about 360°.

In connection with one or more of the previously mentioned preferred refinements, it is preferred, if the second shaft portion is rotatable with respect to a stationary portion of the shaft.

By virtue of this configuration, the rotary movement is achieved in a manner which is advantageously simple in construction by the fact, that the second shaft portion when rotated relative to the stationary shaft portion entrains the first shaft portion, the distal head and thereby the optical imaging system.

In a further preferred refinement, a control mechanism is provided to control the pivoting movement of the optical imaging system about the first and/or the at least one second pivot axis.

The advantage of a control mechanism is that the single movements of the optical imaging system about the first and/or at least one second pivot axis and, if provided, about the longitudinal axis of the shaft, can be controlled by the user of the endoscope on demand as the need arises.

In this connection, it is preferred if the control mechanism is configured such that it can control the pivoting movement of the optical imaging system about the first pivot axis independently from the pivoting movement about the at least one second pivot axis and vice versa.

The advantage of this measure is that in cases where only a change of the direction of view in a small angle range, for example in an angle range of less than 90° from the longitudinal axis as required, it is sufficient to pivot the optical imaging system about the first pivot axis, without the need to additionally pivot the optical imaging system about the at least one second pivot axis. This can be advantageous, if the observation area is very narrow and not much wider than the outer diameter of the distal end of the endoscope shaft where the optical imaging system is arranged, because the pivoting movement of the optical imaging system about the first pivot axis does not require an additional lateral space, while such additional lateral space is necessary for a pivoting movement of the optical Imaging system about the second pivot axis.

In a further preferred refinement, the control mechanism comprises at least one gear having a first wheel which meshes with a second wheel fixed to the distal head.

As an alternative or additional preferred refinement, the control mechanism comprises a belt drive in order to pivot the distal head relative to the first shaft portion.

Both the afore-mentioned refinements have the advantage to provide control mechanisms which can be very small in construction and even be designed in miniaturized form so that these kinds of control mechanisms have the advantage not to enlarge the size of the distal region of the endoscope.

Further, it is preferred if the control mechanism comprises at least an electric motor for driving the gear or the belt drive mentioned before.

Nowadays, electric motors are available in miniaturized size which are suited as a power source for the control mechanism in the endoscope according to the invention.

In a similar manner, and providing the same advantages, it is preferred, if the control mechanism comprises a gear or belt drive to control the pivoting movement of the first shaft portion with respect to the second shaft portion, and if the control mechanism comprises at least an electric motor to drive the gear or the belt drive for pivoting the first shaft portion with respect to the second shaft portion.

Finally, with respect to the rotary movement of the optical imaging system about the longitudinal axis of the shaft, it is also preferred, if the control mechanism comprises a gear to control the rotating movement of the second shaft portion with respect to the stationary portion of the shaft, and, if the control mechanism comprises at least an electric motor for driving the gear for rotating the second shaft portion with respect to the remainder of the shaft.

Nevertheless, other preferred control mechanisms which can be provided as control mechanism for pivoting the optical imaging system about the first and/or at least one second pivot axis and/or for rotating it about the longitudinal axis of the shaft, can be magnetic, pneumatic, hydraulic control mechanisms, or control mechanisms, which act just mechanically such as via pull-and push rods.

Further, the distal head containing the optical imaging system can be supported in magnetic bearings, air cushion bearings or the like.

The one or more electric motors mentioned before in connection with the control mechanism preferably is or are a step motor.

The advantage of a step motor is that also very small movements of the optical imaging system can be controlled in a very fine and precise manner.

In a further preferred refinement, the endoscope according to the invention further comprises an illuminating system for transmitting light into the observation area, the illuminating system being pivotable about the first and at least one second pivot axis together with the optical imaging system.

The advantage of this measure is, that the illuminating system always follows the movement of the optical imaging system, thus ensuring that the region of the observation area which is actually observed, is always sufficiently illuminated.

In this connection, it is preferred if the illuminating system comprises a light source having at least one light emitting diode (LED) arranged adjacent the optical imaging system, and/or if the illuminating system comprises a light source configured as a ring or at least as a partial ring surrounding or at least partially surrounding a light entrance window of the optical imaging system.

It is to be understood that the ring shaped illuminating system can be comprised of a plurality of adjacent LED's or of a single LED in ring shape.

Such LED light sources are obtainable in miniaturized size, and, therefore, are very suited as illuminating system for the endoscope according to the invention.

Further advantages and features will be apparent from the following description and the accompanying drawings.

It is to be understood, that the afore-mentioned features and those features to be explained below are not only applicable in the mentioned combinations, but also in other combinations or in isolation, without departing from the scope of the invention.

BRIEF DESCRIPTION OF THE DRAWINGS

Preferred embodiments of the invention are illustrated in the accompanying drawings and will be described hereinafter with reference to the drawings. In the drawings.

DETAILED DESCRIPTION OF PREFERRED EXEMPLARY EMBODIMENTS

FIGS. 1 through 8 show an endoscope 10 in its distal region.

The endoscope 10 can be an endoscope for medical purposes or an endoscope for industrial purposes.

Figure 1:
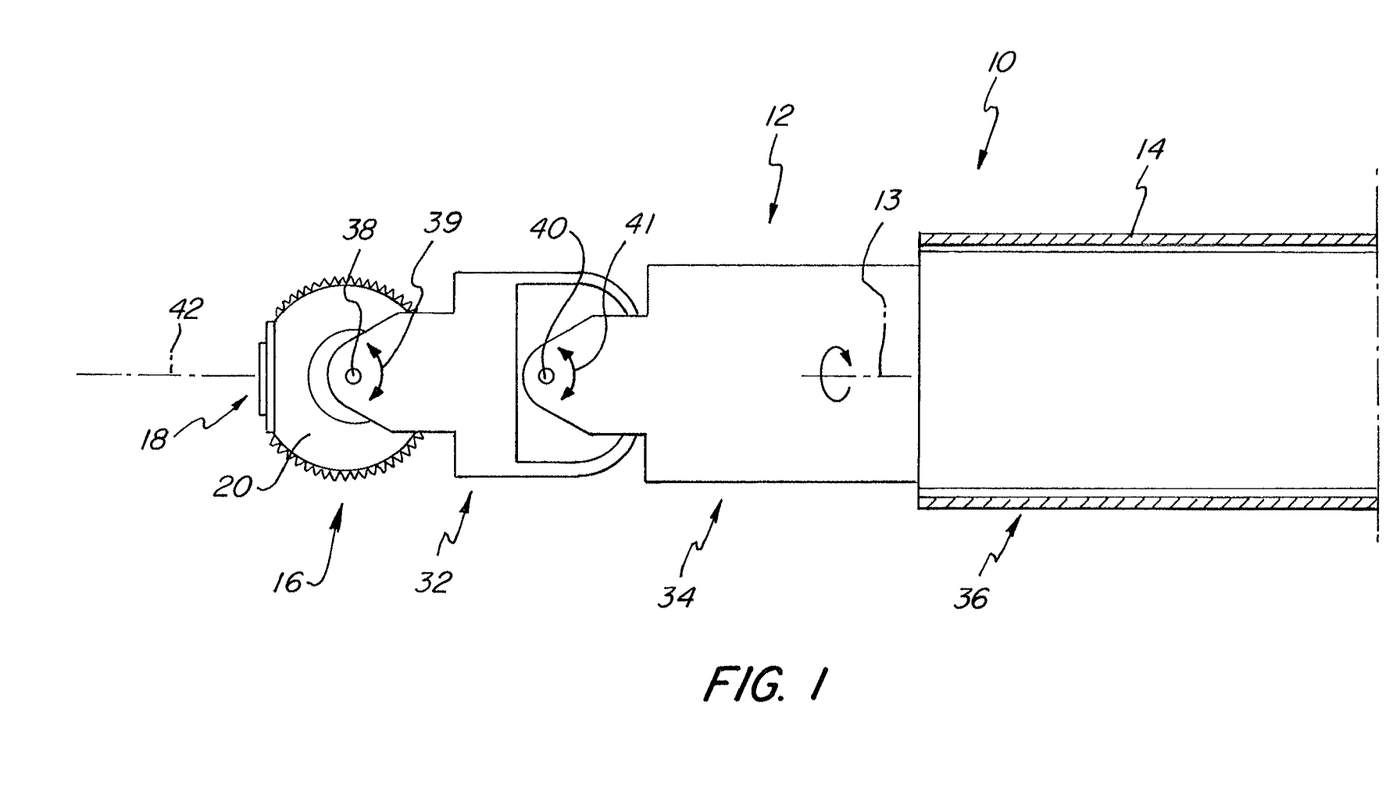
FIG. 1 shows a distal region of an endoscope in a side view, partially in longitudinal section, in an operating condition providing an angle of view of 0° with respect to a longitudinal axis of the endoscope shaft.
Figure 8:
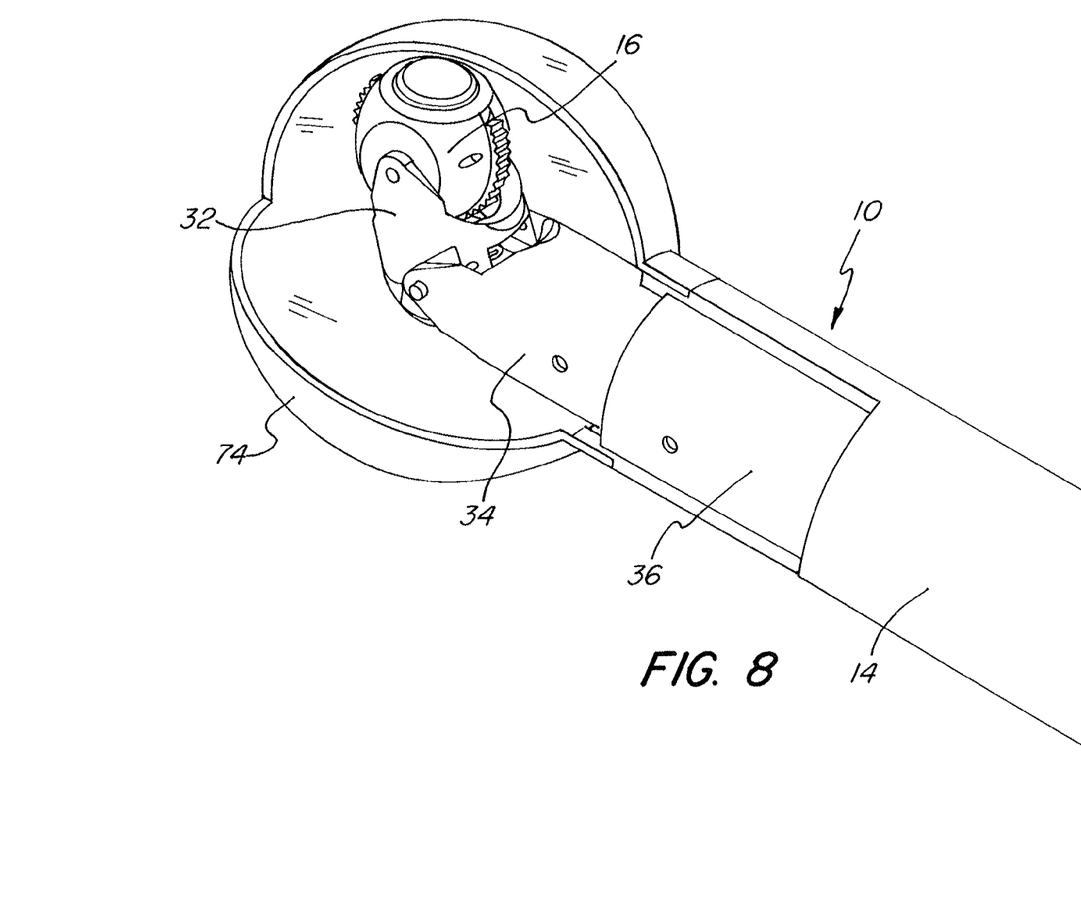
FIG. 8 is a representation of the endoscope in the previous Figures, partially in a longitudinal section, additionally showing an outer shaft and a glass ball surrounding the inner shaft portions and the distal head of the endoscope.

The endoscope 10 comprises an elongated shaft 12 having a longitudinal axis 13. At least a distal end of the shaft 12 is rigid. As illustrated in FIGS. 8 and 1, shaft 12 comprises an outer shaft 14 which extends to a proximal end (not shown) of the endoscope. The outer shaft 14 is a stationary portion of the shaft 12, as will be described in more detail below. Only for the reason of simplicity of illustration, the outer shaft 14 has been shown as transparent part, while in practical cases, the outer shaft 14 is made of steel, for example.

Figure 3:
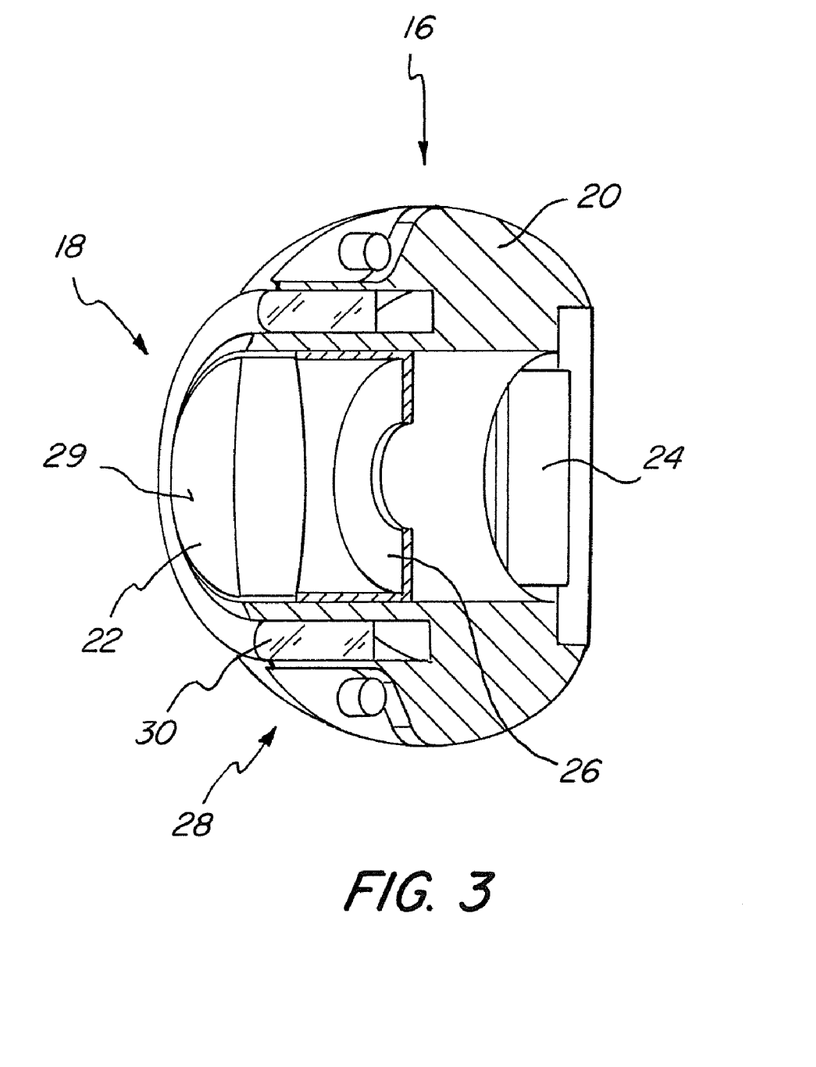
FIG. 3 shows a perspective sectional view of a distal head of the endoscope containing an optical Imaging system and an illuminating system of the endoscope.

The distal end of the endoscope 10 comprises a rigid distal head 16 which comprises or contains an optical imaging system 18, which is illustrated in more detail in FIG. 3.

With reference to FIG. 3, the optical imaging system 18 comprises an imaging optics 22 which is configured in the illustrated embodiment as an objective lens with imaging capabilities. The optical imaging system 18 further comprises an electronic image pick-up 24, which is configured in the present embodiment as a CCD-chip. An aperture stop 26 is arranged between the imaging optics 22 and the image pick-up 24.

The imaging optics 22, the image pick-up 24 and the aperture stop 26 form a miniaturized video camera which is completely incorporated in the distal head 16 of the endoscope 10.

The distal head 16 comprises a substantially ball-shaped housing 20 for housing the imaging optics 22, the aperture stop 26 and the image pick-up 24.

Further, one or more receiver coils can be arranged in the distal head for receiving inductively coupled-in energy and control signals, and a transmission system which transmits image signals from the image pick-up outwards for further processing.

Further, the endoscope 10 comprises an illuminating system 28 which is also arranged in the distal head 16. The illuminating system 28 comprises a light source 30 configured as a ring which surrounds a light entrance window 29 of the optical imaging system 18, i.e. the light source 30 surrounds the objective lens forming the imaging optics 22 of the optical imaging system 18.

Again with reference to FIGS. 1 through 8, the distal end of the endoscope 10 further comprises a first shaft portion 32 arranged proximally to distal head 16 and connected thereto, and a second shaft portion 34 arranged proximally to first shaft portion 32 and connected thereto.

A third shaft portion 36 is arranged proximally to the second shaft portion 34.

Again, only for the sake of illustration, the shaft portions 32 and 34 and 36 have been shown as transparent parts in FIGS. 4 through 7 in order to have sight onto inner parts of the endoscope 10.

The distal head 16 is connected to the first shaft portion 32 in articulated fashion via a pin connection so that the distal head 16 is pivotable about a first pivot axis 38 according to a double arrow 39.

The first shaft portion 32 in turn is connected to the second shaft portion 34 in articulated manner via another pin connection so that the first shaft portion 34 and thereby the distal head 16 is pivotable about a second pivot axis 40 according to a double arrow 41.

By virtue of the articulated connection of the distal head 16 to the first shaft portion 32 and of the first shaft portion 32 to the second shaft portion 34, the optical imaging system 18 is pivotable about the first pivot axis 38 as well as about the second pivot axis 40 according to the double arrows 39 and 41.

As can be seen in FIG. 1 for example, the second pivot axis 40 is spaced from the first pivot axis 38 in direction of the longitudinal axis 13 of the endoscope shaft 12. The distance between the first pivot axis 38 and the second pivot axis 40 is approximately equal to or somewhat larger than the outer diameter of the shaft 12 of the endoscope 10.

The first pivot axis 38 and the second pivot axis 40 both run about transversely to the longitudinal axis 13 of the shaft 12 and are about parallel to one another.

The optical imaging system 18 is pivotable about the first and second pivot axis 38, 40 in opposite directions with respect to the longitudinal axis 13.

Figure 4:
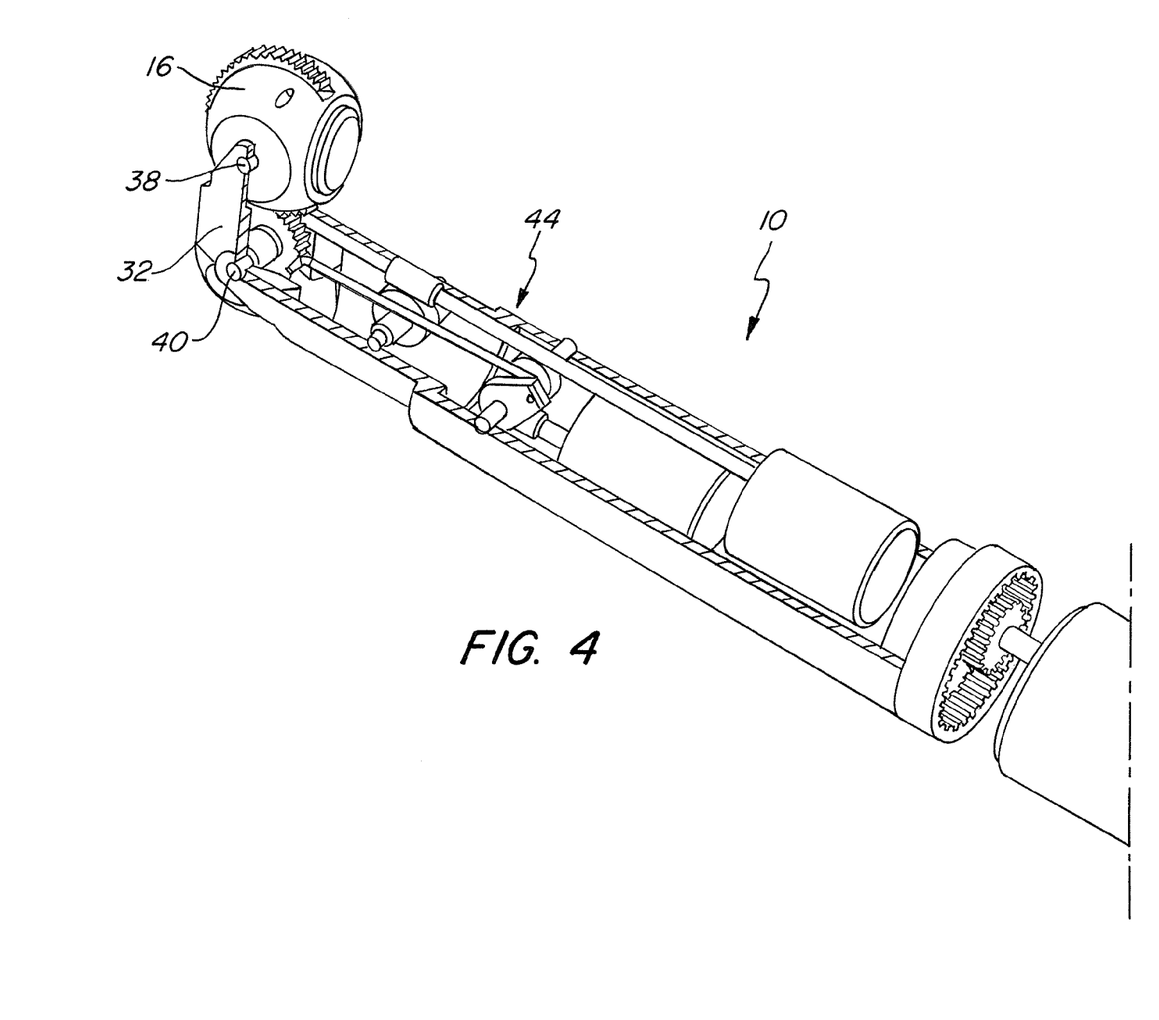
FIG. 4 shows the endoscope in FIGS. 1 and 2, partially in a longitudinal section, in a representation where a control mechanism for pivoting the optical imaging system of the endoscope about a first and second pivot axis can be seen while the endoscope is in an operating condition where an angle of view is about 180° with respect to the longitudinal axis of the shaft.

The pivot axes 38 and 40 allow for a pivoting movement of the optical imaging system 18 in one plane, which is the plane of the drawing in FIG. 1, over an overall pivot range of ±180° from the longitudinal axis 13 of the shaft 12. Thus, the direction of view or the angle of view can be changed from 0° as shown in FIG. 1, where the direction of view illustrated by line 42 in FIG. 1 coincides with the longitudinal axis 13 of the shaft 12 of the endoscope 10, to both sides of the longitudinal axis 13 by ±180°. An angle of view of 180° with respect to the longitudinal axis 13 of the shaft 12 of the endoscope 10 means a backward view as shown in FIG. 4.

The single pivot range of the pivoting movement of the optical imaging system 18 about the first pivot axis 38 and about the second pivot axis 40, respectively, is at least about ±90°. For example, in FIG. 4 the distal head 16 is pivoted about the first pivot axis 38 by an angle of about 90°, and the first shaft portion 32 is pivoted about the second pivot axis 40 by an angle of about 90°, too, leading to an overall pivot range of about 180°.

Figure 2:
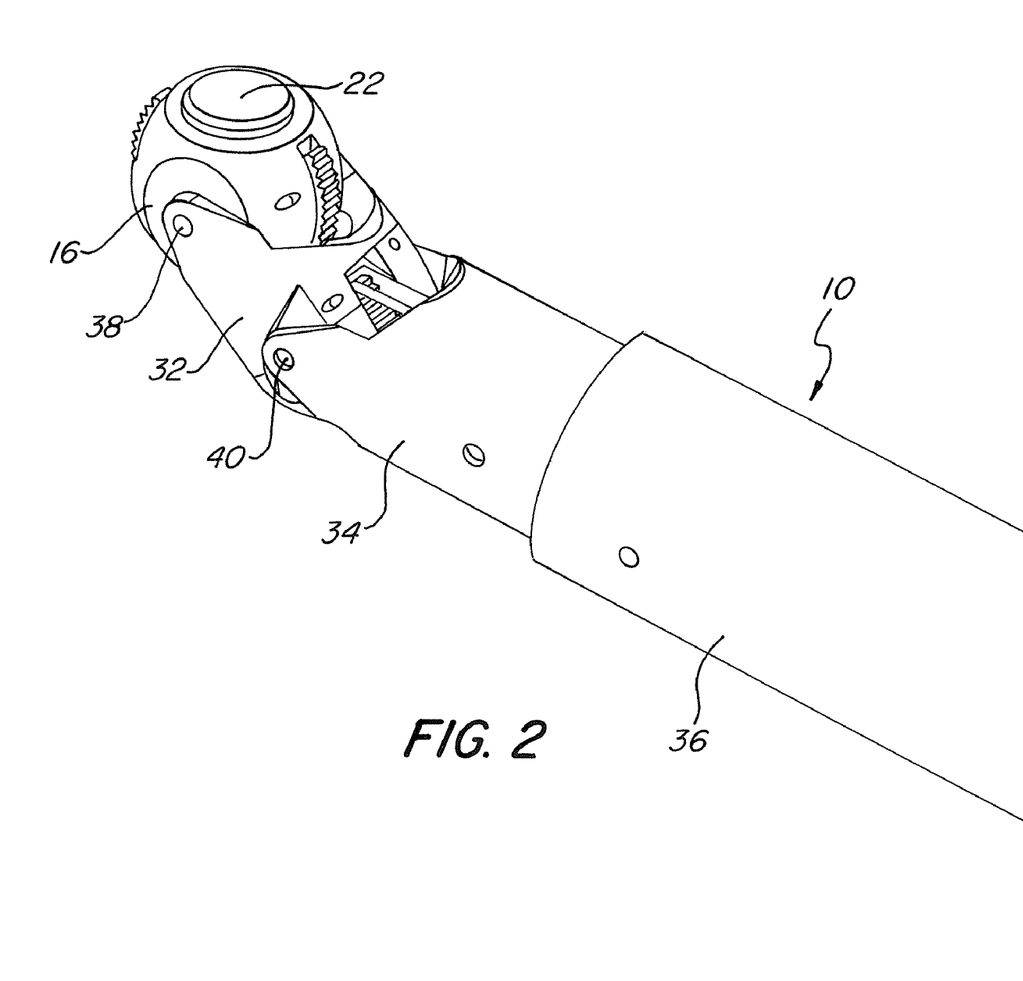
FIG. 2 shows the endoscope in FIG. 1 in a perspective view in an operating condition providing an angle of view of about 90° with respect to the longitudinal axis of the endoscope shaft.

In another instance, as can be seen in FIG. 2, the optical imaging system 18 is pivoted about the first pivot axis 38 and the second pivot axis 40 by an overall angle of about 90° with respect to the longitudinal axis 13 of the shaft 12 of the endoscope 10, wherein the distal head 16 is pivoted about the first pivot axis 38 by an angle of about 45°, and the first shaft portion 32 is pivoted about the second pivot axis 40 by an angle of about 45°, too. However, the same pivot angle of 90° of the optical imaging system 18 with respect to the longitudinal axis 13 can be achieved by pivoting the distal head 16 about the first pivot axis 38 by an angle of about 90°, while the first shaft portion 32 is in its 0° position, i.e. aligned with the second shaft portion 34.

In general, it is sufficient if the distal head 16 is pivotable about the first pivot axis 38 by a maximum angle of about 90°, and the first shaft portion 32 is pivotable about the second pivot axis 40 by a maximum pivot angle of about 90°, too. However, other combinations of maximum pivot angles about the first and second pivot axis 38 and 40 are conceivable.

The optical imaging system 18 is not only pivotable in a plane in order to change the direction of view, but is also rotatable with respect to the shaft 12 about the longitudinal axis 13 thereof. This is accomplished by the fact that the second shaft portion 34 is rotatable about the longitudinal axis 13 with respect to the outer shaft 14 of the endoscope 10.

By rotating the second shaft portion 34 about the longitudinal axis 13, the distal head 16 and the first shaft portion 32 are rotated about the longitudinal axis 13 together with the second shaft portion 34. Rotation of the optical imaging system 18 about the longitudinal axis 13 changes the direction of view in a plane perpendicular to the longitudinal axis 13 (in the 90° case) or the direction of view is swept over a cone the aperture angle of which is determined by the pivot angle of the optical imaging system 18 about the first and second pivot axis 38, 40.

The maximum rotary angle of the second shaft portion 34 about the longitudinal axis 13 is at least 360°.

In total, the optical imaging system 18 can be moved by pivoting the distal head 16 about the first and second pivot axis 38, 40 and by rotating the second shaft portion 34 about the longitudinal axis 13 in such a manner that the direction of view can take any arbitrary orientation within the entire solid angle of about $4\pi$ without the need of replacing, rotating or moving the endoscope 10 from its position.

In the following, a control mechanism is described with respect to FIGS. 4 through 7 which enables the optical imaging system 18 to change its orientation as described before.

As depicted in FIG. 4, the endoscope 10 comprises a control mechanism 44 to control the pivoting movement of the optical imaging system 18 about the first pivot axis 38 and the at least one second pivot axis 40.

Figure 5:
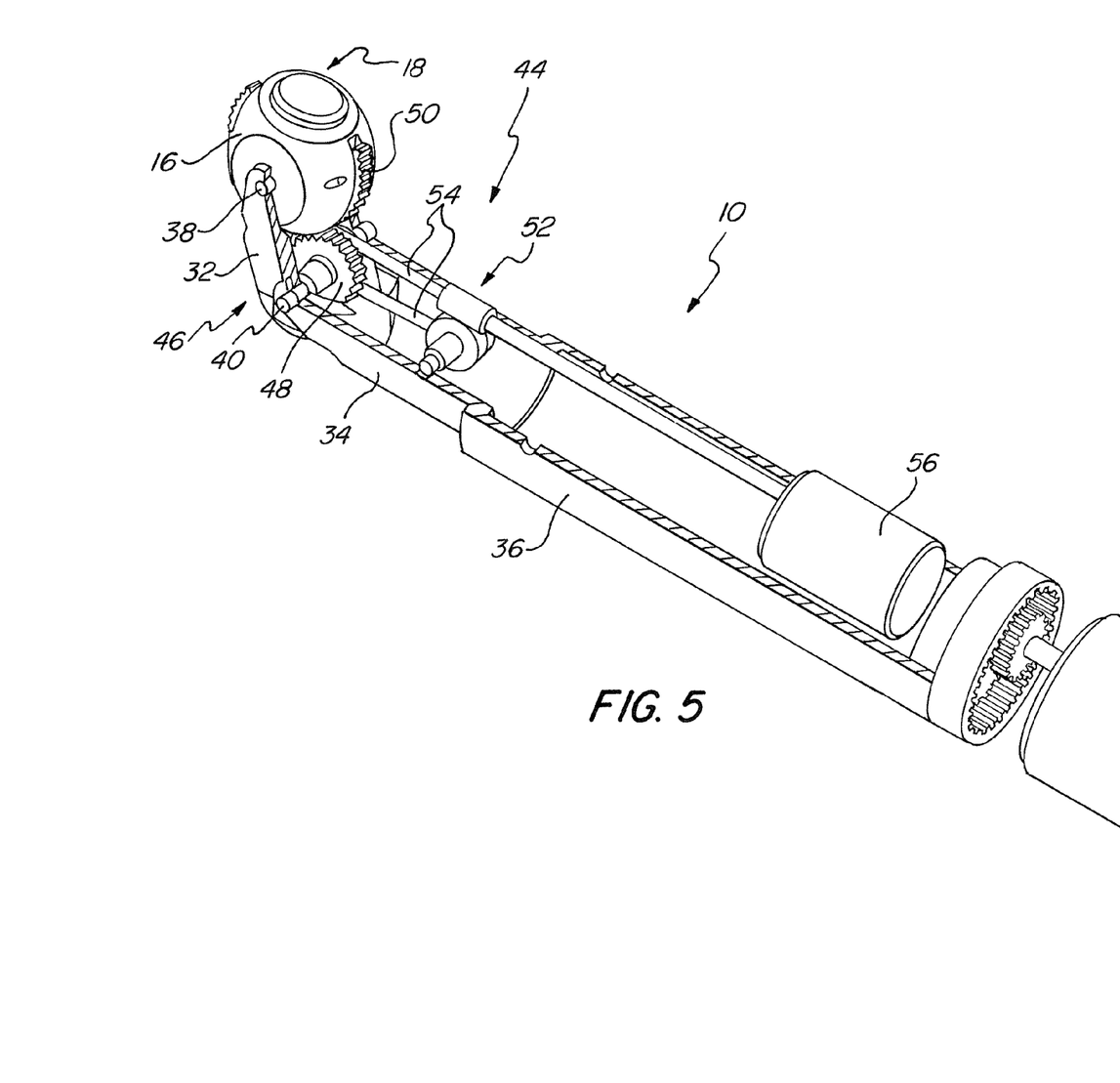
FIG. 5 is a representation similar to FIG. 4, wherein the control mechanism for the pivoting movement of the optical imaging system about the second pivot axis has been omitted and the endoscope is in the operating condition similar to FIG. 2.

FIG. 5 shows only such parts of the control mechanism which are provided to control the pivoting movement of the optical imaging system 18 about the first pivot axis 38. For that purpose, the control mechanism 44 comprises a first gear 46, having a first wheel 48 which is fixed to the first shaft portion 32. In order to be more precise, the first wheel 48 is arranged on the axle or pin forming the second pivot axis 40, such that the first wheel 48 can freely rotate about that pin forming the second pivot axis 40.

The first wheel 48 is a toothed wheel which meshes with a second wheel 50 which is fixed to the distal head 16. The second wheel 50 is arranged concentrically with respect to the first pivot axis 38. The second wheel 50 is a toothed wheel, too. The second wheel 50 is formed as a circumferentially partial ring which is embedded in the housing 20 of the distal head 16.

The control mechanism 44 comprises a second gear 52 which is configured as a worm gear which is connected to the first gear 46 by means of a belt 54 in order to drive, i.e. to rotate, the first wheel 48 of the first gear 46.

The control mechanism 44 further comprises an electric motor to drive the second gear 52 and thereby the first gear 46 in order to pivot the distal head 16 and thereby the optical imaging system 18 about the first pivot axis 38. The electric motor 56, which is a step motor, is arranged in the third portion 36 of the shaft 12 of the endoscope 10.

Figure 6:
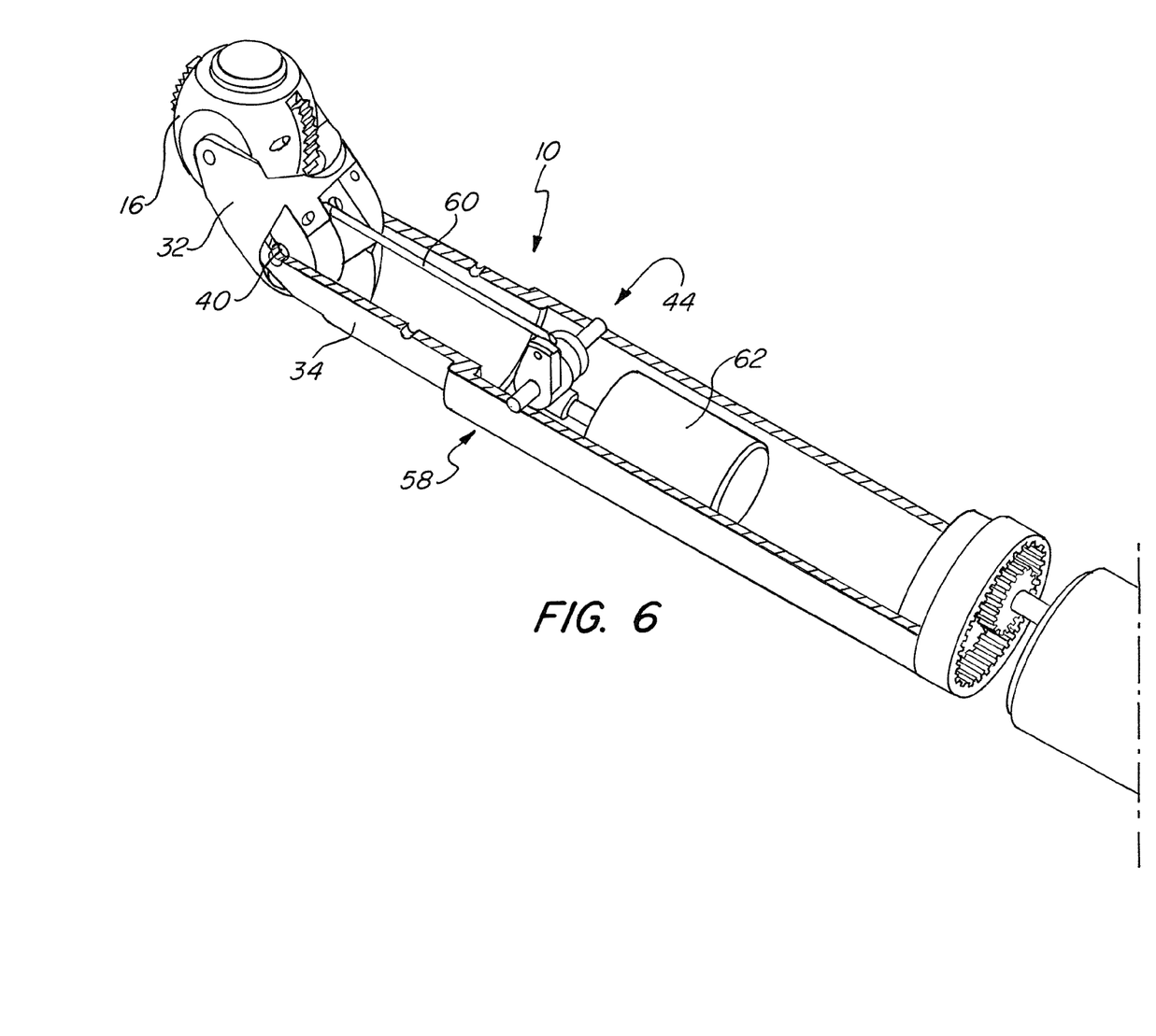
FIG. 6 is a representation similar to FIG. 4, wherein the control mechanism for the pivoting movement of the optical imaging system about the first pivot axis has been omitted, and the endoscope is in an operating condition similar to FIG. 2.

With reference to FIG. 6, the control mechanism 44 comprises a third gear 58 in order to pivot the first shaft portion 32, thereby the distal head 16 and thereby the optical imaging system 18 about the second pivot axis 40.

The third gear 58 is configured as a worm gear similar to the second gear 52. The third gear 58 is connected to the first shaft portion 32 through a push and pull rod 60 which engages the first shaft portion 32 distally spaced from the second pivot axis 40.

The control mechanism 44 comprises a second electric motor 62 in order to drive the third gear 58, and, thereby, to pivot the first shaft portion 32 about the second pivot axis 40.

As follows from the preceding description, the control mechanism 44 is configured such that it can control the pivoting movement of the optical imaging system 18 about the first pivot axis 38 independently from the pivoting movement about the at least one second pivot axis 40 and vice versa.

Figure 7:
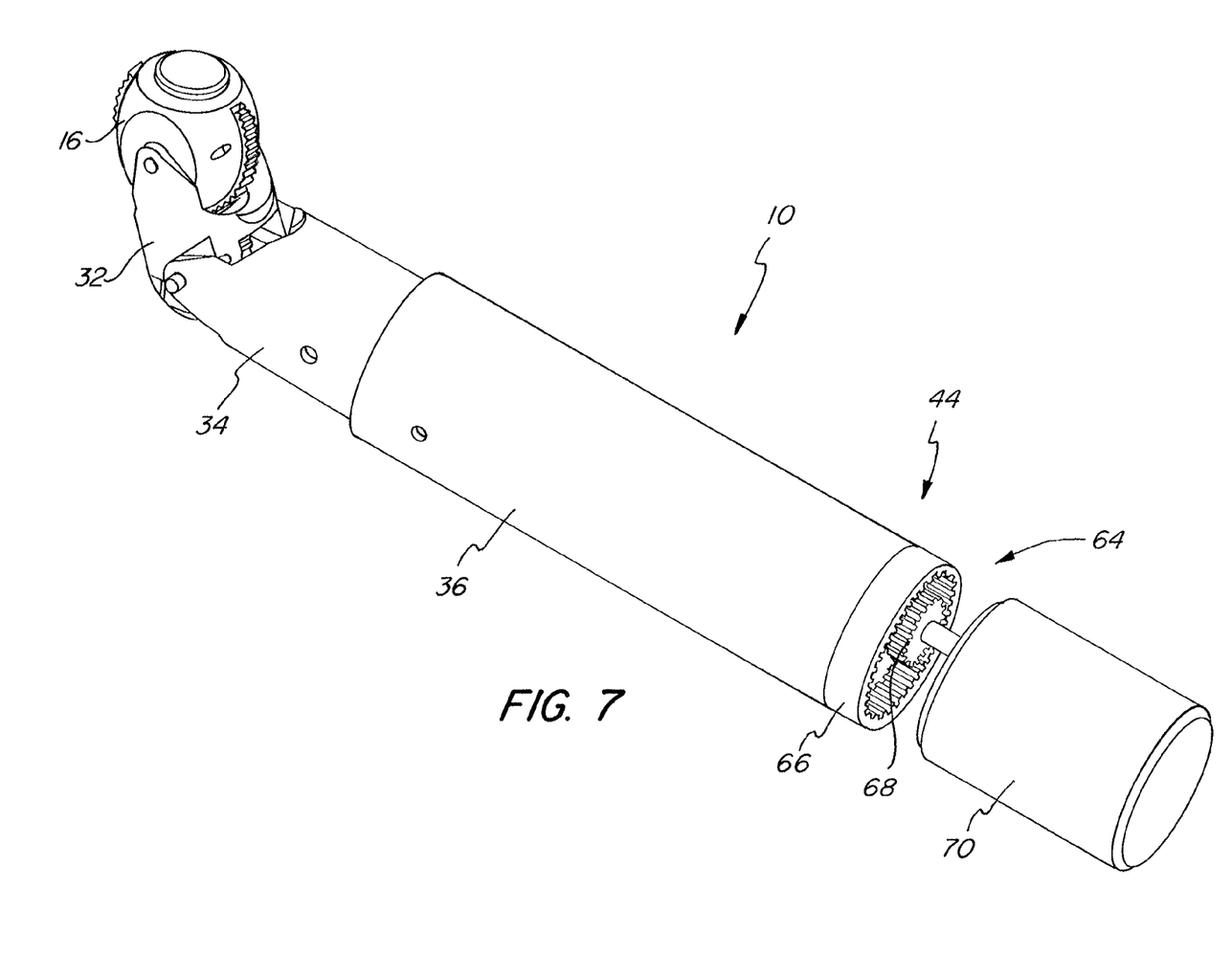
FIG. 7 is a representation similar to FIGS. 5 and 6, wherein the control mechanism for rotating the optical imaging system about the longitudinal axis of the endoscope shaft is illustrated.

With reference to FIG. 7, the control mechanism 44 further comprises a fourth gear 64 to control the rotating movement of the second shaft portion 34 with respect to the remainder of the shaft 12, in the present case with respect to the outer shaft 14 of the endoscope 10. The fourth gear 64 comprises a first wheel 66 fixed to the third shaft portion 36 and having a toothing on its inner side, which meshes with a second wheel 68, having an outer toothing, accordingly. The second wheel 68 is driven by a third electric motor 70, which is a step motor.

FIG. 7 shows all components of the control mechanism 44 described before in place in the endoscope 10.

Figure 9:
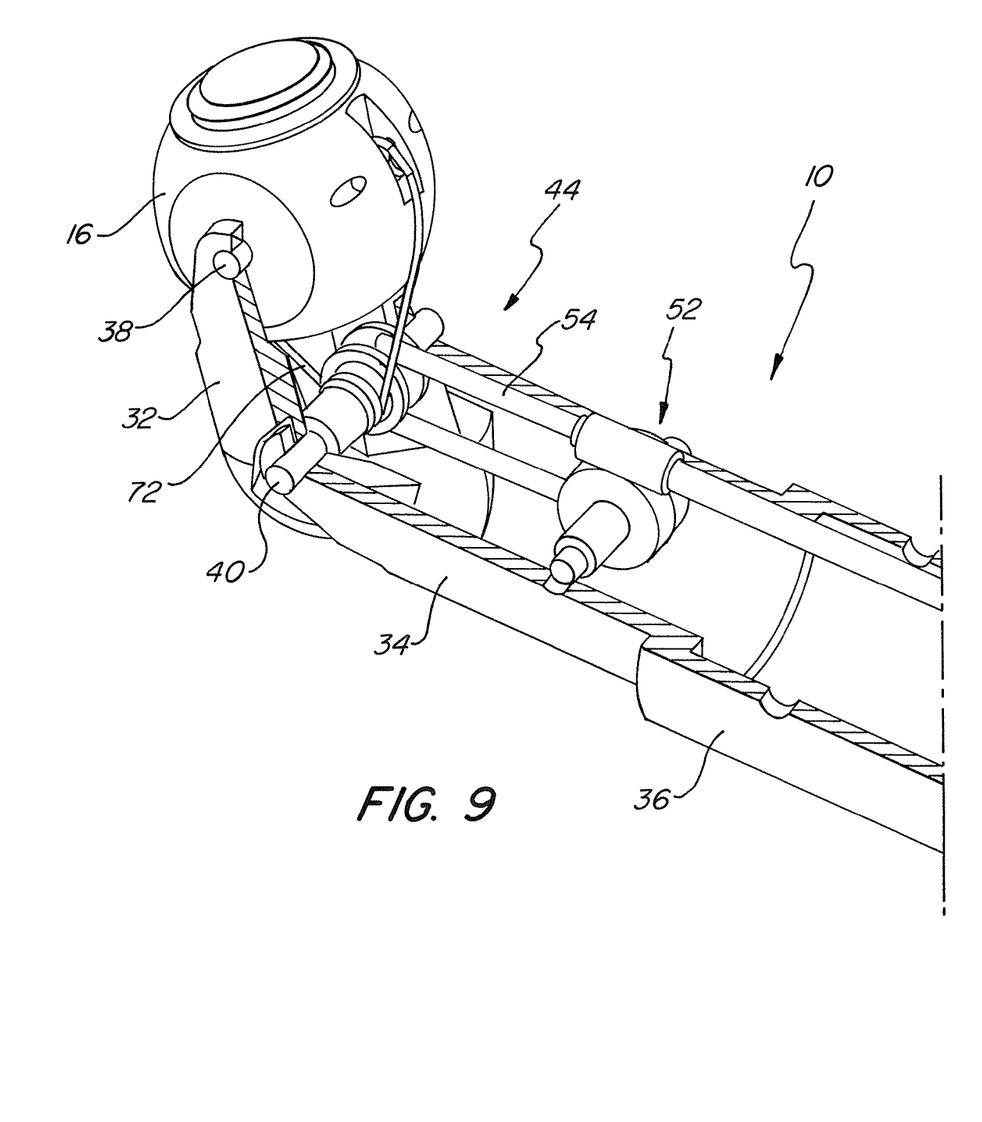
FIG. 9 shows an alternative embodiment of the control mechanism for pivoting the optical imaging system about the first pivot axis.

FIG. 9 shows a slightly modified embodiment of the control mechanism 44 for pivoting the distal head 16 about the first pivot axis 38. Instead of the first wheel 48 and the second wheel 50, the control mechanism 44 comprises a belt which is fed around the pin of the second pivot axis 40, and which is driven by the second gear 52 and the belt 54.

FIG. 8 shows the complete distal region of the endoscope 10 where the third shaft portion 36 and all the parts of the control mechanism 44 are surrounded by the outer shaft 14 which extends (not shown) to the proximal end of the endoscope 10.

At its distal end, the outer shaft 14 is connected with a glass ball which surrounds the distal head 16, the first shaft portion and the second shaft portion 34. The glass ball 74 is arranged such that in each orientation of the distal head 16 the direction of view is perpendicular to the surface of the glass ball in order to avoid a displacement of the direction of view due to refraction.

In other embodiments (not shown), the glass ball 74 can be replaced by a transparent flexible tube, for example.

What is claimed is:

1. An endoscope comprising
an elongated shaft having a substantially rigid distal end and a longitudinal axis, said distal end being formed by a distal head having a substantially ball-shaped housing, said shaft further having a first shaft portion arranged proximally from and connected to said ball-shaped housing and a second shaft portion arranged proximally from and connected to said first shaft portion,
an optical imaging system at least partially arranged in said ball-shaped housing and being fixed thereto for receiving light from an observation area,
wherein said ball-shaped housing is pivotable with respect to said first shaft portion about a first pivot axis running about transversely to said longitudinal axis of said shaft and substantially through a center of said ball-shaped housing, wherein said first shaft portion is pivotable with respect to said shaft about at least a second pivot axis spaced from said first pivot axis and running about transversely to said longitudinal axis of said shaft, such that an overall pivot range of said optical imaging system about said first and said at least second pivot axis is at least 150° from said longitudinal axis of said shaft.

2. The endoscope of claim 1, wherein said overall pivot range is at least about 180° from said longitudinal axis of said shaft.

3. The endoscope of claim 1, wherein said optical imaging system is pivotable about at least one of said first and said at least second pivot axis from said longitudinal axis in opposite directions.

4. The endoscope of claim 1, wherein said optical imaging system is pivotable about said first pivot axis in the range of at least about 70° to about 110° and about said at least second pivot axis in a range of at least about 40° to about 110°.

5. The endoscope of claim 1, wherein said first pivot axis and said at least second pivot axis are about parallel with respect to one another.

6. The endoscope of claim 1, wherein said optical imaging system comprises an electronic image pick-up and an imaging optics for imaging an object to be viewed onto said image pick-up, said image pick-up and said imaging optics being arranged in said distal head.

7. The endoscope of claim 1, wherein said optical imaging system is rotatable about said longitudinal axis of said shaft.

8. The endoscope of claim 7, wherein a range of rotation of said optical imaging system is about 360°.

9. The endoscope of claim 1, wherein said second shaft portion is rotatable with respect to a stationary portion of said shaft.

10. The endoscope of claim 1, wherein a control mechanism is provided to control pivoting movement of said optical imaging system about at least one of said first and said at least second pivot axis.

11. The endoscope of claim 10, wherein said control mechanism is configured such that it can control pivoting movement of said optical imaging system about said first pivot axis independently from pivoting movement about at least one second pivot axis.

12. The endoscope of claim 10, wherein said control mechanism comprises at least one gear having a first wheel which meshes with a second wheel fixed to said ball-shaped housing to control pivoting movement of said ball-shaped housing about said first pivot axis.

13. The endoscope of claim 12, wherein said control mechanism comprises at least one electric motor for driving said gear.

14. The endoscope of claim 13, wherein said electric motor is a step motor.

15. The endoscope of claim 10, wherein said control mechanism comprises a belt drive in order to pivot said ball-shaped housing about said first pivot axis.

16. The endoscope of claim 15, wherein said control mechanism comprises at least one electric motor for driving said belt drive.

17. The endoscope of claim 10, wherein said control mechanism comprises at least one of a gear and belt drive to control pivoting movement of said first shaft portion with respect to said second shaft portion.

18. The endoscope of claim 17, wherein said control mechanism comprises at least one electric motor to drive said at least one of said gear and said belt drive for pivoting said first shaft portion with respect to said second shaft portion.

19. The endoscope of claim 18, wherein said electric motor is a step motor.

20. The endoscope of claim 1, wherein said second shaft portion is rotatable with respect to a stationary portion of said shaft about said longitudinal axis of said shaft, wherein a control mechanism is provided for rotating said second shaft portion with respect to said stationary portion of said shaft, and wherein said control mechanism comprises a gear to control rotating movement of said second shaft portion with respect to said stationary portion of said shaft.

21. The endoscope of claim 20, wherein said control mechanism comprises at least one electric motor for driving said gear for rotating said second shaft portion.

22. The endoscope of claim 21, wherein said electric motor is a step motor.

23. The endoscope of claim 1, further comprising an illuminating system for transmitting light into said observation area, said illuminating system being pivotable about said first and said at least second pivot axis together with said optical imaging system.

24. The endoscope of claim 23, wherein said illuminating system comprises a light source having at least one light emitting diode arranged adjacent to said optical imaging system.

25. The endoscope of claim 23, wherein said illuminating system comprises a light source configured at least partially as a ring, which at least partially surrounds a light entrance window of said optical imaging system.

* * * * *